(12) United States Patent
Kidron

(10) Patent No.: US 10,350,162 B2
(45) Date of Patent: Jul. 16, 2019

(54) METHODS AND COMPOSITIONS FOR ORAL ADMINISTRATION OF EXENATIDE

(71) Applicant: Oramed Ltd., Jerusalem (IL)

(72) Inventor: Miriam Kidron, Jerusalem (IL)

(73) Assignee: Oramed Ltd., Jerusalem (IL)

( * ) Notice: Subject to any disclaimer, the term of this patent is extended or adjusted under 35 U.S.C. 154(b) by 61 days.

(21) Appl. No.: 13/855,346

(22) Filed: Apr. 2, 2013

(65) Prior Publication Data

US 2013/0195939 A1  Aug. 1, 2013

Related U.S. Application Data

(62) Division of application No. 12/990,097, filed as application No. PCT/IL2009/000461 on May 3, 2009, now abandoned.

(60) Provisional application No. 61/071,538, filed on May 5, 2008.

(51) Int. Cl.

| A61K 9/48 | (2006.01) |
|---|---|
| A61K 9/00 | (2006.01) |
| A61K 9/28 | (2006.01) |
| A61K 31/202 | (2006.01) |
| A61K 31/22 | (2006.01) |
| A61K 38/26 | (2006.01) |
| A61K 38/57 | (2006.01) |
| A61K 38/56 | (2006.01) |

(52) U.S. Cl.
CPC .......... *A61K 9/0053* (2013.01); *A61K 9/0031* (2013.01); *A61K 9/2846* (2013.01); *A61K 9/4866* (2013.01); *A61K 31/202* (2013.01); *A61K 31/22* (2013.01); *A61K 38/26* (2013.01); *A61K 38/56* (2013.01); *A61K 38/57* (2013.01)

(58) Field of Classification Search
None
See application file for complete search history.

(56) References Cited

U.S. PATENT DOCUMENTS

| 4,579,730 A | 4/1986 | Kidron et al. |
|---|---|---|
| 5,034,415 A | 7/1991 | Rubin |
| 5,206,219 A | 4/1993 | Desai |
| 5,665,700 A | 9/1997 | Cho et al. |
| 5,824,638 A | 10/1998 | Burnside et al. |
| 6,692,766 B1 | 2/2004 | Rubinstein et al. |
| 6,761,903 B2 | 7/2004 | Chen et al. |
| 6,858,576 B1 | 2/2005 | Young et al. |
| 7,404,973 B2 | 7/2008 | Konwinski et al. |
| 9,186,412 B2 | 11/2015 | Kidron et al. |
| 9,259,456 B2 | 2/2016 | Kidron |
| 2002/0032171 A1 | 3/2002 | Chen et al. |
| 2003/0118610 A1 | 6/2003 | Stern et al. |
| 2004/0097410 A1 | 5/2004 | Zheng et al. |
| 2005/0143303 A1 | 6/2005 | Quay et al. |
| 2005/0232981 A1 | 10/2005 | Ben-Sasson |
| 2006/0018874 A1 | 1/2006 | Radhakrishnan et al. |
| 2006/0045868 A1 | 3/2006 | Meezan et al. |
| 2006/0045869 A1 | 3/2006 | Meezan et al. |
| 2006/0234913 A1 | 10/2006 | Arbit et al. |
| 2006/0264401 A1 | 11/2006 | Campbell et al. |
| 2006/0286129 A1 | 12/2006 | Sarubbi |
| 2006/0293232 A1 | 12/2006 | Levy et al. |
| 2007/0077283 A1 | 4/2007 | Quay et al. |
| 2007/0086972 A1 | 4/2007 | Birnbaum |
| 2007/0087957 A1 | 4/2007 | Kidron |
| 2011/0014247 A1 | 1/2011 | Kidron |
| 2011/0046053 A1 | 2/2011 | Kidron |
| 2011/0166062 A1 | 7/2011 | DiMarchi et al. |
| 2014/0377344 A1 | 12/2014 | Hershko et al. |
| 2015/0017238 A1 | 1/2015 | Kidron |
| 2015/0335715 A1 | 11/2015 | Kidron et al. |
| 2016/0206703 A1 | 7/2016 | Kidron |

FOREIGN PATENT DOCUMENTS

| CA | 1223200 A1 | 6/1987 |
|---|---|---|
| CA | 2621577 A1 | 3/2007 |
| CN | 101095942 A | 2/2008 |
| EP | 0351651 A2 | 1/1990 |
| IL | 68769 A | 2/1986 |
| JP | 02-250823 | 10/1990 |
| JP | 09-208485 A | 8/1997 |
| JP | 10-330287 A | 12/1998 |
| JP | 00-050793 A | 2/2000 |
| JP | 2001-240558 | 4/2001 |
| JP | 2001-240558 A | 9/2001 |
| JP | 2005-525308 | 8/2005 |
| JP | 2011-515458 | 5/2011 |
| KR | 01-0069433 A | 7/2001 |
| KR | 2001/0069322 A | 7/2001 |

(Continued)

OTHER PUBLICATIONS

Joslin Diabetes Center (retrieved from http://www.joslin.org/info/will_diabetes_go_away.html on Apr. 22, 2015, 2 pages).*
WebMD (retrieved from http://www.webmd.com/diabetes/is-there-a-diabetes-cure on Apr. 22, 2015, 3 pages).*
Cure talk (retrieved from http://trialx.com/curetalk/2012/05/type-2-diabetes-difficult-to-treat-in-children-new-study/ on Apr. 22, 2015, 2 pages).*
The Observer (retrieved from http://observer.com/2014/02/tough-to-swallow-paper-trail-behind-breakthrough-leads-to-penny-stock-profiteers/ on Apr. 22, 2015, 5 pages).*
Agarwal, et al.; "Oral Delivery of Proteins: Effect of Chicken and Duck Ovomucoid on the Stability of Insulin in the Presence of α-Chymotrypsin and Trypsin"; Pharm. Pharmacol. Commun.; (2000); 6: 223-227.

(Continued)

*Primary Examiner* — Karlheinz R. Skowronek
*Assistant Examiner* — Ronald T Niebauer
(74) *Attorney, Agent, or Firm* — Sterne, Kessler, Goldstein & Fox P.L.L.C.

(57) ABSTRACT

This invention provides compositions comprising a byetta, fish oil, and a protease inhibitor, method for treating diabetes mellitus, comprising administering same, and methods for oral or rectal administration of a byetta.

11 Claims, 2 Drawing Sheets

Specification includes a Sequence Listing.

(56) References Cited

FOREIGN PATENT DOCUMENTS

| RU | 2104715 C1 | 2/1998 |
|---|---|---|
| WO | WO 91/14454 A1 | 10/1991 |
| WO | WO 97/03688 | 2/1997 |
| WO | WO 00/24424 A1 | 7/2000 |
| WO | WO 03/057170 A2 | 7/2003 |
| WO | WO 2007/029238 | 3/2007 |
| WO | WO 09/118722 A2 | 10/2009 |
| WO | WO 2009/136392 A2 | 11/2009 |

OTHER PUBLICATIONS

Bar-On, H., et al.; "Enteral Administration of Inslin in the Rat"; Br. J. Pharmac. (1981); 73: 21-24.
Bendayan, et al.; "Morpho-cytochemical and biochemical evidence for insulin absorption by the rat ileal epithelium"; Diabetologia (1990); 33: 197-204.
Bendayan, et al.; "Biochemical and morpho-cytochemical evidence for the intestinal absorption of insulin in control and diabetic rats. Comparison between the effectiveness of duodenal and colon mucosa"; Diabetologia (1994); 37: 119-126.
Carino, et al.; "Oral insulin delivery"; Advanced Drug Delivery Review (1999); 35: 249-257.
Cernea, et al.; "Comparison of pharmacokinetic and harmacodynamics properties of single-dose oral insulin spray and subcutaneous insulin injection in healthy subjects using the euglycemic clamp technique"; Clinical Therapeutics (2004); 26(12): 2084-2091.
Cernea, et al.; "Dose-Response Relationship of Oral Insulin Spray in Healthy Subjects"; Diabetes Care (2005); 28(6): 1353-1357.
Cernea, et al.; "Dose-Response Relationship of an Oral Insulin Spray in Six Patients with Type 1 Diabetes: A Single-Center, Randomized, Single-Blind, 5-Way Crossover Study"; Clinical Therapeutics (2005); 27(10): 1562-1570.
Cole, et al.; "Challenges and opportunities in the encapsulation of liquid and semi-solid formulations into capsules for oral administration"; Advanced Drug Delivery Reviews (2008); 60: 747-756.
Cournarie, et al.; "Insulin-loaded W/O/W multiple emulsions: comparison of the performances of systems prepared with medium-chain-triglycerides and fish oil"; Euro. J. of Pharmaceutics and BioPharmaceutics; (2004); 58(3): 477-482.
Gowthamarajan & Kulkarni; Oral Insulin—Fact or Fiction—Possibilities of Achieving Oral Delivery for Insulin; Resonance (2003); 38-46.
Hays, et al.; "Prevention and Treatment of Type 2 Diabetes: Current Role of Lifestyle, Natural Product, and Pharmacological Interventions"; Pharmacol. Ther. (2008); 118(2): 181-191.
Heine, et al.; "Exenatide versus Insulin Glargine in Patients with Suboptimally Controlled Type 2 Diabetes"; American College of Physicians—Annals of Internal Medicine 2005; 143(8): 559-569.
Iyer, et al.; "Oral insulin—a review of current status"; Diabetes, Obesity and Metabolism (2010); 12: 179-185.
Kidron, et al.; "A novel per-oral insulin formulation: proof of concept study in non-diabetic subjects"; Diabetic Medicine (2004); 21: 354-357.
Kidron, et al.; "Extended exposure to an oral insulin formulation yields decreased insulin secretion in Type II diabetes subjects"; Diabetes Technology Meeting Nov. 11-13, 2010.
Lasserson, et al.; "Optimal insulin regimens in type 2 diabetes mellitus: systematic review and meta-analyses"; Diabetologia (2009); 52: 1990-2000.
Li and Deng; "Oil-based formulation for oral delivery of insulin"; J. Pharmacy Pharmacol 2004; 56: 1101-1107.
Ma, et al.; "In vitro and in vivo evaluation of a novel oral insulin formulation"; Acta Pharmacologica Sinica (2006); 27(10): 1382-1388.
Mack, et al. "Antibestiy action of peripheral exenatide (exendin-4) in rodents: effects on food intake, body weight, metabolic status and side-effect measures"; International Journal of Obesity (2006); 30: 1332-1340.

Maher, S. et al.; "Safety and efficacy of sodium caprate in promoting oral drug absorption: from in vitro to the clinic"; Advanced Drug Delivery Reviews; (2009); 61: 1427-1449.
Miyagawa, Jun-ichiro; Med Sci Digest 2008 34(4):147-150.
Morishita, et al.; "Hypoglycemic effect of novel oral microspheres of insulin with protease inhibitor in normal and diabetic rats"; Int. J. of Pharma; (1992); 78: 9-16.
Nissan, et al.; "Intestinal absorption of low molecular weight heparin in animals and human subjects"; Haemostasis (2000); 30: 225-232.
Onuki, et al.; "In vivo effects of highly purified docosahexaenoic acid on rectal insulin absorption"; Int. J. of Pharmaceutics; (2000); 198(2): 147-156.
Ray Dirks Research; "Novo Nordisk Sitting on $2 Billion in Cash May Look to Acquire Oramed or ISIS for Oral Insulin"; May 31, 2012.
Raz, et al.; "Rectal Administration of Insulin"; Israel Journal of Medical Sciences (1984); 20: 173-175.
Sherman, "Oramed Enrolls First Patient in its Phase 2a U.S. Oral Insulin Clinical Trial"; Jul. 8, 2013.
Silva-Cunha et al.; "W/O/W multiple emulsions of insulin containing a protease inhibitor and an absorption enhancer: preparation, characterization and determination of stability towards proteases in vitro"; Int. J. of Pharmaceutics; (1997); 158(1): 79-89.
Ziv, et al.; "Bile Salts Promote the Absorption of Insulin from the Rat Colon"; Life Sciences (1981); 29: 803-809.
Ziv, et al.; "Absorption of Protein via the Intestinal Wall a Quantitative Model"; Biochemical Pharmacology (1987); 36(7): 1035-1039.
Ziv, et al.; "Oral administration of insulin in solid form to nondiabetic and diabetic dogs"; Journal of Pharmaceutical Sciences (1994); 83(6): 792-794.
International Search Report and Written Opinion for International Application No. PCT/IL2009/000461 dated Sep. 25, 2009.
International Preliminary Report on Patentability for International Application No. PCT/IL2009/000461 dated Nov. 9, 2010.
[No Author Listed] Worthington Biochemical Corporation (2016; Trypsin inhibitors C.A.S.: 9035-81-1. On the web at worthington-biochem.com/Ti/default.html.
Birk, Trypsin and chymotrypsin inhibitors from soybeans.Methods Enzymol. 1976;45:700-7.
Chiquette et al., Treatment with exenatide once weekly or twice daily for 30 weeks is associated with changes in several cardiovascular risk markers. Vasc Health Risk Manag. 2012;8:621-9. doi: 10.2147/VHRM.S37969. Epub Nov. 12, 2012.
Eldor et al., A Single-Blind, Two-Period Study to Assess the Safety and Pharmacodynamics of an Orally Delivered GLP-1 Analog (Exenatide) in Healthy SubjectsAmerican Diabetes Association 70th Annual Scientific Sessions, Jun. 25-29, 2010A, Orlando, Florida.
Eldor et al., Open-label study to assess the safety and pharmacodynamics of five oral insulin formulations in healthy subjects.Diabetes Obes Metab. Mar. 2010;12(3):219-23. doi: 10.1111/j.1463-1326.2009.01153.x.
Eldor et al., Novel glucagon-like peptide-1 analog delivered orally reduces postprandial glucose excursions in porcine and canine models. J Diabetes Sci Technol. Nov. 1, 2010;4(6):1516-23.
Gershanik et al., Self-dispersing lipid formulations for improving oral absorption of lipophilic drugs. European Journal of Pharmaceuticals and Biopharmaceutics. 2000;50:179-188.
Griffin,Calculation of HLB Values of Non-Ionic Surfactants. J Soc Cosmetic Chemists 5:259 (1954).
Koide et al., Studies on soybean trypsin inhibitors. 3. Amino-acid sequences of the carboxyl-terminal region and the complete amino-acid sequence of soybean trypsin inhibitor (Kunitz).Eur J Biochem. Feb. 1, 1973;32(3):417-31.
Koide et al., The amino acid sequence of soybean trypsin inhibitor. J. Biochem. 1972;71:165-7.
Martinez-Colubi et al., Switching to darunavir/ritonavir monotherapy (DRV/r mx): effect on kidney function and lipid profile. J Int AIDS Soc. Nov. 11, 2012;15(6):18348. doi:10.7448/IAS.15.6.18348.

(56) References Cited

OTHER PUBLICATIONS

Miyashita et al., Hepatoprotective effect of tamoxifen on steatosis and non-alcoholic steatohepatitis in mouse models. J Toxicol Sci. 2012;37(5):931-42.

Morishita et al. Novel oral microspheres of insulin with protease inhibitor protecting from enzymatic degradation. International Journal of Pharmaceutics. 78 (1992) 1-7.

Nadeau et al., Treatment of non-alcoholic fatty liver disease with metformin versus lifestyle intervention in insulin-resistant adolescents. Pediatr Diabetes. Feb. 2009;10(1):5-13. doi: 10.1111/j.1399-5448.2008.00450.x. Epub Aug. 20, 2008.

Ozawa et al., The reactive site of trypsin inhibitors.J Biol Chem. Sep. 10, 1966;241(17):3955-61.

Park et al., Oral protein delivery: Current status and future prospect. Reactive and Functional Polymers. 71 (2011) 280-287.

Ryan et al., Assessment of the severity of hypoglycemia and glycemic lability in type 1 diabetic subjects undergoing islet transplantation. Diabetes. Apr. 2004;53(4):955-62.

Shyangdan et al., Insulin sensitisers in the treatment of non-alcoholic fatty liver disease: a systematic review. Health Technol Assess. Nov. 2011;15(38):1-110. doi: 10.3310/hta15380.

Siepmann et al., Blends of aqueous polymer dispersions used for pellet coating: importance of the particle size. J Control Release. Jul. 20, 2005;105(3):226-39.

Sprecher et al., Molecular cloning, expression, and partial characterization of two novel members of the ovalbumin family of serine proteinase inhibitors. J Biol Chem. Dec. 15, 1995;270(50):29854-61.

Sun et al., Gene structure, chromosomal localization, and expression of the murine homologue of human proteinase inhibitor 6 (PI-6) suggests divergence of PI-6 from the ovalbumin serpins. J Biol Chem. Jul. 7, 1995;270(27):16089-96.

Tesauro et al., Effects of GLP-1 on forearm vasodilator function and glucose disposal during hyperinsulinemia in the metabolic syndrome. Diabetes Care. Mar. 2013;36(3):683-9. doi: 10.2337/dc12-0763. Epub Oct. 15, 2012.

Umezawa, Structures and activities of protease inhibitors of microbial origin.Methods Enzymol. 1976;45:678-95.

Yeboah et al., A rapid purification method for soybean Bowman-Birk protease inhibitor using hydrophobic interaction chromatography. Protein Expression and Purification. 1996;7:309-14.

\* cited by examiner

METHODS AND COMPOSITIONS FOR ORAL ADMINISTRATION OF EXENATIDE

RELATED APPLICATION

This application is divisional of U.S. patent application Ser. No. 12/990,097, filed Oct. 28, 2010, which is a U.S.C. 371 National Phase Application of International Application No. PCT/IL2009/000461, filed May 3, 2009, which claims priority from U.S. Provisional Patent Application No. 61/071,538, filed May 5, 2008, the contents of which are incorporated herein by reference.

FIELD OF INVENTION

This invention provides oral compositions comprising Exenatide, and a method for administering same.

BACKGROUND OF THE INVENTION

Due to improved biotechnology, the accessibility of biologically active peptides to the pharmaceutical industry has increased considerably. However, a limiting factor in the development of peptide drugs is the relative ineffectiveness when given perorally. Almost all peptide drugs are parenterally administered, although parenterally administered peptide drugs are often connected with low patient compliance.

Exenatide is a glucagon-like peptide (GLP-1) agonist that was approved by the Food and Drug Administration for adjunctive therapy when patients with type 2 diabetes have not been optimally controlled on metformin. It is an incretin mimetic and potentiates exenatide secretion while inhibiting glucagon secretion and slowing gastric emptying.

Exenatide (marketed as Byetta) is manufactured and marketed by Amylin Pharmaceuticals and Eli Lilly and Company. Exenatide is a synthetic version of exendin-4, a hormone in the saliva of the Gila monster, a lizard native to several Southwestern American states. Typical human responses to exenatide include improvements in the initial rapid release of endogenous insulin, suppression of pancreatic glucagon release, delayed gastric emptying, and reduced appetite—all of which function to lower blood glucose. Unlike sulfonylureas and meglitinides, exenatide increases insulin synthesis and secretion in the presence of glucose only, lessening the risk of hypoglycemia. Byetta is also being used by some physicians to treat insulin resistance.

Exenatide augments pancreas response (i.e. increases insulin secretion) in response to eating meals; the result is the release of a higher, more appropriate amount of insulin that helps lower the rise in blood sugar from eating. Once blood sugar levels decrease closer to normal values, the pancreas response to produce insulin is reduced; however, other drugs (like injectable insulin) are effective at lowering blood sugar, but can "overshoot" their target and cause blood sugar to become too low, resulting in the dangerous condition of hypoglycemia.

Exenatide also suppresses pancreatic release of glucagon in response to eating, which helps stop the liver from overproducing sugar when it is unneeded, which prevents hyperglycemia (high blood sugar levels).

Exenatide helps slow down gastric emptying and thus decreases the rate at which meal-derived glucose appears in the bloodstream.

Exenatide has a subtle yet prolonged effect to reduce appetite and thus may prevent weight gain. Most people using Exenatide slowly lose weight, and generally the greatest weight loss is achieved by people who are the most overweight at the beginning of exenatide therapy. Clinical trials have demonstrated that the weight reducing effect continues at the same rate through 2.25 years of continued use. When separated into weight loss quartiles, the highest 25% experience substantial weight loss and the lowest 25% experience no loss or small weight gain.

Exenatide reduces liver fat content. Fat accumulation in the liver or non-alcoholic fatty liver disease (NAFLD) is strongly related with several metabolic disorders, in particular low HDL cholesterol and high triglycerides, present in patients with type 2 diabetes. It became apparent that exenatide reduced liver fat in mice and more recently in man.

Exenatide is a polypeptide consisting of 39 amino acids with a molecular weight of 4186.6. Ex vivo human placental perfusion studies detected minimal levels on the fetal side (fetal: maternal ratio 0.017).

Exenatide is currently administered as a subcutaneous injection, generally concomitantly with a sulfonylurea or metformin. Although it has a modest effect on lowering fasting glucose levels, it markedly reduces postprandial glucose.

The present invention addresses the need for an alternate solution for administration of exenatide.

SUMMARY OF THE INVENTION

This invention provides, in one embodiment, a composition comprising an exenatide and a protease inhibitor, wherein the composition is an oral pharmaceutical composition or a rectal pharmaceutical composition.

In another embodiment, the present invention provides a method for oral or rectal administration of exenatide to a subject, whereby a substantial fraction of exenatide retains its activity after absorption, through an intestinal mucosal barrier or through a rectal tissue of said subject, comprising administering orally or rectally to a subject a pharmaceutical composition comprising said exenatide.

In another embodiment, the present invention provides a method for treating diabetes mellitus in a subject, comprising administering orally or rectally to a subject a pharmaceutical composition comprising exenatide, thereby treating diabetes mellitus.

In another embodiment, the present invention provides a method for reducing food intake in a subject, comprising administering orally or rectally to a subject a pharmaceutical composition comprising exenatide, thereby reducing food intake in a subject.

In another embodiment, the present invention provides a method for reducing gastric motility in a subject, comprising administering orally or rectally to a subject a pharmaceutical composition comprising exenatide, thereby reducing gastric motility in a subject.

In another embodiment, the present invention provides a method for lowering plasma glucagon in a subject, comprising administering orally or rectally to said subject a pharmaceutical composition comprising exenatide, thereby lowering plasma glucagon in a subject.

DETAILED DESCRIPTION OF THE INVENTION

Figure 1:
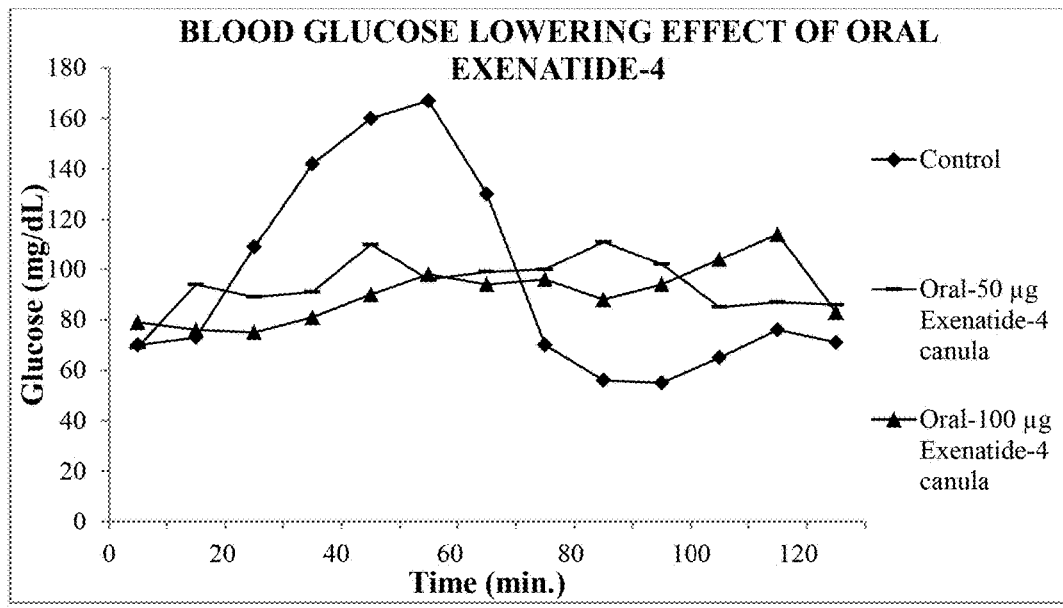
FIG. 1 is a graph showing the blood glucose lowering effect of an Exendin-4-oral dosage form compared to control in dogs.

This invention provides compositions and methods comprising exenatide and an omega-3 fatty acid. In another embodiment, the present invention provides compositions and methods comprising exenatide and a protease inhibitor. In another embodiment, the present invention provides compositions and methods comprising exenatide and an enhancer such as EDTA and salts thereof such as Na-EDTA. In another embodiment, the present invention provides compositions and methods comprising exenatide and Na-EDTA. In another embodiment, the present invention provides compositions and methods comprising exenatide, omega-3 fatty acid, and Na-EDTA. In another embodiment, the present invention provides oral compositions comprising exenatide. In another embodiment, the present invention provides oral compositions comprising exenatide and Na-EDTA. In another embodiment, the present invention provides oral compositions comprising exenatide, omega-3 fatty acid, and Na-EDTA. In another embodiment, the present invention provides rectal compositions comprising exenatide and Na-EDTA. In another embodiment, the present invention provides rectal compositions comprising exenatide, omega-3 fatty acid, and Na-EDTA. In one embodiment, the present invention provides a composition comprising exenatide and an omega-3 fatty acid. As provided herein (Examples), such compositions have utility in the oral administration of exenatide, whereby the exenatide is absorbed by the intestines into the bloodstream in an active form.

In another embodiment, byetta is the proprietary name for the active ingredient exenatide. In another embodiment, exenatide is designated AC2993 and is a synthetic exendin-4. In another embodiment, exenatide is a 39-amino acid peptide. In another embodiment, exenatide comprises the amino acid sequence: HGEGTFTSDLSKQMEEEAVR-LFIEWLKNGGPSSGAPPPS (SEQ ID NO: 1). In another embodiment, exenatide containing the amino acid sequence of SEQ ID NO: 1. In another embodiment, exenatide comprises an amino acid sequence having at least 70% identity to SEQ ID NO: 1. In another embodiment, exenatide comprises an amino acid sequence having at least 80% identity to SEQ ID NO: 1. In another embodiment, exenatide comprises an amino acid sequence having at least 90% identity to SEQ ID NO: 1. In another embodiment, exenatide comprises an amino acid sequence having at least 95% identity to SEQ ID NO: 1. In another embodiment, exenatide comprises an amino acid sequence having at least 99% identity to SEQ ID NO: 1.

In another embodiment, exenatide oral or rectal formulation of the invention is effective for diabetic therapy. In another embodiment, exenatide oral or rectal formulation of the invention enhances insulin secretion. In another embodiment, exenatide enhances glucose-dependent insulin secretion. In another embodiment, exenatide oral or rectal formulation of the invention suppresses high glucagon secretion. In another embodiment, exenatide oral or rectal formulation of the invention slows of gastric-emptying rate. In another embodiment, exenatide oral or rectal formulation of the invention binds to the pancreatic glucagon-like peptide-1 (GLP-1) receptor. In another embodiment, exenatide oral or rectal formulation of the invention reduces food intake. In another embodiment, exenatide oral or rectal formulation of the invention causes weight loss. In another embodiment, exenatide oral or rectal formulation of the invention comprises an insulin-sensitizing effect. In another embodiment, exenatide oral or rectal formulation of the invention improves glycemic control among patients with type 2 diabetes. In another embodiment, exenatide oral or rectal formulation of the invention improves glycemic control among patients with type 2 diabetes treated with sulfonylureas or metformin, alone or in combination.

In another embodiment, exenatide is Exendin-4 comprising 53% amino acid sequence overlap with mammalian GLP-1. In another embodiment, oral or rectal formulation comprising exenatide is resistant to DPP-IV degradation. In another embodiment, oral or rectal formulation comprising exenatide reduces postprandial glycemia. In another embodiment, oral or rectal formulation comprising exenatide induces the release of insulin and Amylin. In another embodiment, oral or rectal formulation comprising exenatide is not associated with weight gain. In another embodiment, oral or rectal formulation comprising exenatide reduces postprandial serum triglyceride concentrations. In another embodiment, oral or rectal formulation comprising exenatide cause less adverse events than an injectable formulation comprising exenatide. In another embodiment, treatment with oral or rectal formulation comprising exenatide does not cause nausea. In another embodiment, treatment with oral or rectal formulation comprising exenatide cause only mild nausea. In another embodiment, treatment with oral or rectal formulation comprising exenatide does not cause gastroparesis.

In another embodiment, the amount of Exenatide in a formulation as described herein is 10 mcg to 1 mg. In another embodiment, the amount of Exenatide in a formulation as described herein is 10 mcg to 25 mcg. In another embodiment, the amount of Exenatide in a formulation as described herein is 25 mcg to 50 mcg. In another embodiment, the amount of Exenatide in a formulation as described herein is 50 mcg to 60 mcg. In another embodiment, the amount of Exenatide in a formulation as described herein is 60 mcg to 70 mcg. In another embodiment, the amount of Exenatide in a formulation as described herein is 70 mcg to 80 mcg. In another embodiment, the amount of Exenatide in a formulation as described herein is 80 mcg to 90 mcg. In another embodiment, the amount of Exenatide in a formulation as described herein is 90 mcg to 100 mcg. In another embodiment, the amount of Exenatide in a formulation as described herein is 100 mcg to 110 mcg. In another embodiment, the amount of Exenatide in a formulation as described herein is 110 mcg to 125 mcg. In another embodiment, the amount of Exenatide in a formulation as described herein is 125 mcg to 150 mcg. In another embodiment, the amount of Exenatide in a formulation as described herein is 150 mcg to 175 mcg. In another embodiment, the amount of Exenatide in a formulation as described herein is 175 mcg to 200 mcg. In another embodiment, the amount of Exenatide in a formulation as described herein is 200 mcg to 220 mcg. In another embodiment, the amount of Exenatide in a formulation as described herein is 220 mcg to 240 mcg. In another embodiment, the amount of Exenatide in a formulation as described herein is 240 mcg to 260 mcg. In another embodiment, the amount of Exenatide in a formulation as described herein is 260 mcg to 300 mcg.

In another embodiment, the amount of Exenatide in a formulation as described herein is 300 mcg to 350 mcg. In another embodiment, the amount of Exenatide in a formulation as described herein is 350 mcg to 400 mcg. In another embodiment, the amount of Exenatide in a formulation as described herein is 400 mcg to 450 mcg. In another embodiment, the amount of Exenatide in a formulation as described herein is 450 mcg to 500 mcg. In another embodiment, the amount of Exenatide in a formulation as described herein is 550 mcg to 600 mcg. In another embodiment, the amount of Exenatide in a formulation as described herein is 600 mcg to 700 mcg. In another embodiment, the amount of Exenatide in a formulation as described herein is 700 mcg to 800 mcg. In another embodiment, the amount of Exenatide in a formulation as described, herein is 800 mcg to 900 mcg. In another embodiment, the amount of Exenatide in a formulation as described herein is 900 mcg to 1 mg.

In another embodiment, the Exenatide formulation as described herein is taken once a day. In another embodiment, the Exenatide formulation as described herein is taken twice a day. In another embodiment, the Exenatide formulation as described herein is taken three times a day. In another embodiment, the Exenatide formulation as described herein is taken four times a day. In another embodiment, the Exenatide formulation as described herein is taken five times a day. In another embodiment, one of skill in the art determines the dosage of Exenatide formulation as described herein. In another embodiment, one of skill in the art determines the daily dose of a Exenatide formulation as described herein. In another embodiment, one of skill in the art determines the daily dosing regimen of a Exenatide formulation as described herein.

In another embodiment, the Exenatide formulation as described herein is taken at least 15 minutes before a meal. In another embodiment, the Exenatide formulation as described herein is taken at least 30 minutes before a meal. In another embodiment, the Exenatide formulation as described herein is taken at least 45 minutes before a meal. In another embodiment, the Exenatide formulation as described herein is taken at least 60 minutes before a meal. In another embodiment, the Exenatide formulation as described herein is taken at least 75 minutes before a meal. In another embodiment, the Exenatide formulation as described herein is taken at least 90 minutes before a meal. In another embodiment, the Exenatide formulation as described herein is taken at least 100 minutes before a meal. In another embodiment, the Exenatide formulation as described herein is taken at least 120 minutes before a meal. In another embodiment, the Exenatide formulation as described herein is taken at least 150 minutes before a meal. In another embodiment, the Exenatide formulation as described herein is taken at least 180 minutes before a meal.

In another embodiment, the Exenatide formulation as described herein reduces the side effects associated with an injectable dosage form comprising Exenatide. In another embodiment, the Exenatide formulation as described herein reduces nausea as a side effect which is associated with an injectable dosage form comprising Exenatide. In another embodiment, the Exenatide formulation as described herein does not induce nausea as a side effect which is associated with an injectable dosage form comprising Exenatide.

In another embodiment, the use of sustained release dosage forms (e.g. sustained release micro encapsulation) enables the treatment frequency to be reduced to once or twice a day. In another embodiment, the exenatide dosage is increased correspondingly with decreasing frequency of administration.

Each amount of exenatide represents a separate embodiment of the present invention. Methods of measuring exenatide levels are well known in the art. In another embodiment, levels of C peptide are measured as well, to determine the relative contributions of endogenous and exogenous exenatide to observed rises in exenatide levels. In another embodiment, exenatide levels are measured by any other method known in the art. Each possibility represents a separate embodiment of the present invention.

In some embodiments, omega-3 fatty acid is derived from vegetable sources such as the seeds of chia, perilla, flax, walnuts, purslane, lingonberry, seabuckthorn, and hemp. In some embodiments, omega-3 fatty acids can also be found in the fruit of the acai palm. In another embodiment, the omega-3 fatty acid has been provided in the form of a synthetic omega-3 fatty acid. In one embodiment, the omega-3 fatty acid of methods and compositions of the present invention has been provided to the composition in the form of a fish oil. In another embodiment, the omega-3 fatty acid has been provided in the form of canola oil. In another embodiment, the omega-3 fatty acid has been provided in the form of flaxseed oil. In another embodiment, the omega-3 fatty acid has been provided in the form of any other omega-3 fatty acid-rich source known in the art. In another embodiment, the omega-3 fatty acid has been provided in the form of a synthetic omega-3 fatty acid. Each form of omega-3 fatty acids represents a separate embodiment of the present invention.

In another embodiment, the omega-3 fatty acid of methods and compositions of the present invention is an omega-3 polyunsaturated fatty acid. In another embodiment, the omega-3 fatty acid is DHA, an omega-3, polyunsaturated, 22-carbon fatty acid also referred to as 4, 7, 10, 13, 16, 19-docosahexaenoic acid. In another embodiment, the omega-3 fatty acid is α-linolenic acid (9, 12, 15-octadecatrienoic acid). In another embodiment, the omega-3 fatty acid is stearidonic acid (6, 9, 12, 15-octadecatetraenoic acid). In another embodiment, the omega-3 fatty acid is eicosatrienoic acid (ETA; 11, 14, 17-eicosatrienoic acid). In another embodiment, the omega-3 fatty acid is eicsoatetraenoic acid (8, 11, 14, 17-eicosatetraenoic acid). In one embodiment, the omega-3 fatty acid is eicosapentaenoic acid (EPA; 5, 8, 11, 14, 17-eicosapentaenoic acid). In another embodiment, the omega-3 fatty acid is eicosahexaenoic acid (also referred to as "EPA"; 5, 7, 9, 11, 14, 17-eicosahexaenoic acid). In another embodiment, the omega-3 fatty acid is docosapentaenoic acid (DPA; 7, 10, 13, 16, 19-docosapenatenoic acid). In another embodiment, the omega-3 fatty acid is tetracosahexaenoic acid (6, 9, 12, 15, 18, 21-tetracosahexaenoic acid). In another embodiment, the omega-3 fatty acid is any other omega-3 fatty acid known in the art. Each omega-3 fatty acid represents a separate embodiment of the present invention.

In another embodiment, compositions of the present invention further comprise a protease inhibitor. In another embodiment, compositions of the present invention further comprise a combination of at least two protease inhibitors. As provided herein, protease inhibitors enhance the ability of omega-3 fatty acids to protect exenatide and facilitate its absorption in the intestine.

In some embodiments, protease inhibitor inhibits the function of peptidases. In one embodiment, protease inhibitors enhance the ability of omega-3 fatty acids to protect the protein of the present invention and facilitate its absorption in the intestine. In some embodiments, the protease inhibitor of the present invention is a protein. In some embodiments, protease inhibitors comprise cysteine protease inhibitors, serine protease inhibitors (serpins), trypsin inhibitors, threonine protease inhibitors, aspartic protease inhibitors, metallo protease inhibitors. In some embodiments, protease inhibitors comprise suicide inhibitor, transition state inhibitor, or chelating agents.

In one embodiment, the protease inhibitor is soybean trypsin inhibitor (SBTI). In another embodiment, the protease inhibitor is AEBSF-HCl. In another embodiment, the inhibitor is (epsilon)-aminocaproic acid. In another embodiment, the inhibitor is (alpha) 1-antichymotypsin. In another embodiment, the inhibitor is antipain. In another embodiment, the inhibitor is antithrombin III. In another embodiment, the inhibitor is (alpha) 1-antitrypsin ([alpha] 1-proteinase inhibitor). In another embodiment, the inhibitor is APMSF-HCl (4-amidinophenyl-methane sulfonyl-fluoride). In another embodiment, the inhibitor is sprotinin. In another embodiment, the inhibitor is benzamidine-HCl. In another embodiment, the inhibitor is chymostatin. In another embodiment, the inhibitor is DPP (diisopropylfluoro-phosphate). In another embodiment, the inhibitor is leupeptin. In another embodiment, the inhibitor is PEFABLOC® SC (4-(2-Aminoethyl)-benzenesulfonyl fluoride hydrochloride). In another embodiment, the inhibitor is PMSF (phenylmethyl sulfonyl fluoride). In another embodiment, the inhibitor is TLCK (1-Chloro-3-tosylamido-7-amino-2-heptanone HCl). In another embodiment, the inhibitor is TPCK (1-Chloro-3-tosylamido-4-phenyl-2-butanone). In another embodiment, the inhibitor is trypsin inhibitor from egg white (Ovomucoid). In another embodiment, the inhibitor is trypsin inhibitor from soybean. In another embodiment, the inhibitor is aprotinin. In another embodiment, the inhibitor is pentamidine isethionate. In another embodiment, the inhibitor is pepstatin. In another embodiment, the inhibitor is guanidium. In another embodiment, the inhibitor is alpha2-macroglobulin. In another embodiment, the inhibitor is a chelating agent of zinc. In another embodiment, the inhibitor is iodoacetate. In another embodiment, the inhibitor is zinc. Each possibility represents a separate embodiment of the present invention.

In another embodiment, the amount of protease inhibitor utilized in methods and compositions of the present invention is 0.1 mg/dosage unit. In another embodiment, the amount of protease inhibitor is 0.2 mg/dosage unit. In another embodiment, the amount is 0.3 mg/dosage unit. In another embodiment, the amount is 0.4 mg/dosage unit. In another embodiment, the amount is 0.6 mg/dosage unit. In another embodiment, the amount is 0.8 mg/dosage unit. In another embodiment, the amount is 1 mg/dosage unit. In another embodiment, the amount is 1.5 mg/dosage unit. In another embodiment, the amount is 2 mg/dosage unit. In another embodiment, the amount is 2.5 mg/dosage unit. In another embodiment, the amount is 3 mg/dosage unit. In another embodiment, the amount is 5 mg/dosage unit. In another embodiment, the amount is 7 mg/dosage unit. In another embodiment, the amount is 10 mg/dosage unit. In another embodiment, the amount is 12 mg/dosage unit. In another embodiment, the amount is 15 mg/dosage unit. In another embodiment, the amount is 20 mg/dosage unit. In another embodiment, the amount is 30 mg/dosage unit. In another embodiment, the amount is 50 mg/dosage unit. In another embodiment, the amount is 70 mg/dosage unit. In another embodiment, the amount is 100 mg/dosage unit.

In another embodiment, the amount of protease inhibitor is 0.1-1 mg/dosage unit. In another embodiment, the amount of protease inhibitor is 0.2-1 mg/dosage unit. In another embodiment, the amount is 0.3-1 mg/dosage unit. In another embodiment, the amount is 0.5-1 mg/dosage unit. In another embodiment, the amount is 0.1-2 mg/dosage unit. In another embodiment, the amount is 0.2-2 mg/dosage unit. In another embodiment, the amount is 0.3-2 mg/dosage unit. In another embodiment, the amount is 0.5-2 mg/dosage unit. In another embodiment, the amount is 1-2 mg/dosage unit. In another embodiment, the amount is 1-10 mg/dosage unit. In another embodiment, the amount is 2-10 mg/dosage unit. In another embodiment, the amount is 3-10 mg/dosage unit. In another embodiment, the amount is 5-10 mg/dosage unit. In another embodiment, the amount is 1-20 mg/dosage unit. In another embodiment, the amount is 2-20 mg/dosage unit. In another embodiment, the amount is 3-20 mg/dosage unit. In another embodiment, the amount is 5-20 mg/dosage unit. In another embodiment, the amount is 10-20 mg/dosage unit. In another embodiment, the amount is 10-100 mg/dosage unit. In another embodiment, the amount is 20-100 mg/dosage unit. In another embodiment, the amount is 30-100 mg/dosage unit. In another embodiment, the amount is 50-100 mg/dosage unit. In another embodiment, the amount is 10-200 mg/dosage unit. In another embodiment, the amount is 20-200 mg/dosage unit. In another embodiment, the amount is 30-200 mg/dosage unit. In another embodiment, the amount is 50-200 mg/dosage unit. In another embodiment, the amount is 100-200 mg/dosage unit.

In another embodiment, the amount of protease inhibitor utilized in methods and compositions of the present invention is 1000 k.i.u. (kallikrein inactivator units)/pill. In another embodiment, the amount is 10 k.i.u./dosage units. In another embodiment, the amount is 12 k.i.u./dosage unit. In another embodiment, the amount is 15 k.i.u./dosage units. In another embodiment, the amount is 20 k.i.u./dosage unit. In another embodiment, the amount is 30 k.i.u./dosage units. In another embodiment, the amount is 40 k.i.u./dosage units. In another embodiment, the amount is 50 k.i.u./dosage units. In another embodiment, the amount is 70 k.i.u./dosage units. In another embodiment, the amount is 100 k.i.u./dosage unit. In another embodiment, the amount is 150 k.i.u./dosage unit. In another embodiment, the amount is 200 k.i.u./dosage units. In another embodiment, the amount is 300 k.i.u./dosage unit. In another embodiment, the amount is 500 k.i.u./dosage units. In another embodiment, the amount is 700 k.i.u./dosage units. In another embodiment, the amount is 1500 k.i.u./dosage unit. In another embodiment, the amount is 3000 k.i.u./dosage unit. In another embodiment, the amount is 4000 kith/dosage unit. In another embodiment, the amount is 5000 k.i.u./dosage unit.

Each amount of protease inhibitor represents a separate embodiment of the present invention.

In another embodiment, the protease targeted by the protease inhibitor of methods and compositions of the present invention is a serine protease. In another embodiment, the protease is trypsin. In another embodiment, the protease is chymotrypsin. In another embodiment, the protease is carboxypeptidase. In another embodiment, the protease is aminopeptidase. In another embodiment, the protease is any other protease that functions in the duodenum or the small intestine. Each possibility represents a separate embodiment of the present invention.

In another embodiment, compositions of the present invention further comprise a substance that enhances absorption of the exenatide through an intestinal mucosal barrier. Such a substance is referred to herein as an "enhancer." As provided herein, enhancers, when used together with omega-3 fatty acids, enhance the ability of exenatide to be absorbed in the intestine.

In one embodiment, the enhancer is didecanoylphosphatidylcholine (DDPC). In one embodiment, the enhancer is a chelating agent such as ethylenediaminetetraacetic acid (EDTA) or egtazic acid EGTA. In a preferred embodiment, EDTA is sodium-EDTA. In some embodiments, the enhancer is NO donor. In some embodiments, the enhancer is a bile acid, glycine-conjugated form of a bile acid, or an alkali metal salt. In one embodiment, absorption enhancement is achieved through utilization of a combination of α-galactosidase and β-mannanase. In some embodiments, the enhancer is a fatty acid such as sodium caprate. In one embodiment, the enhancer is sodium glycocholate. In one embodiment, the enhancer is sodium salicylate. In one embodiment, the enhancer is n-dodecyl-β-D-maltopyranoside. In some embodiments, surfactants serve as absorption enhancer. In one embodiment, the enhancer is chitisan such as N,N,N-trimethyl chitosan chloride (TMC).

In one embodiment, NO donors of the present invention comprise 3-(2-Hydroxy-1-(1-methylethyl)-2-nitrosohydrazino)-1-propanamine, N-ethyl-2-(1-ethyl-hydroxy-2-nitrosohydrazino)-ethanamine, or S-Nitroso-N-acetylpenicillamine In another embodiment, the bile acid is cholic acid. In another embodiment, the bile acid is chenodeoxycholic acid. In another embodiment, the bile acid is taurocholic acid. In another embodiment, the bile acid is taurochenodeoxycholic acid. In another embodiment, the bile acid is glycocholic acid. In another embodiment, the bile acid is glycochenocholic acid. In another embodiment, the bile acid is 3 beta-monohydroxychloric acid. In another embodiment, the bile acid is lithocholic acid. In another embodiment, the bile acid is 5 beta-cholanic acid. In another embodiment, the bile acid is 3,12-diol-7-one-5 beta-cholanic acid. In another embodiment, the bile acid is 3 alpha-hydroxy-12-ketocholic acid. In another embodiment, the bile acid is 3 beta-hydroxy-12-ketocholic acid. In another embodiment, the bile acid is 12 alpha-3 beta-dihydrocholic acid. In another embodiment, the bile acid is ursodesoxycholic acid.

In one embodiment, the enhancer is a nonionic surfactant. In one embodiment, the enhancer is a nonionic polyoxyethylene ether surface active agent (e.g one having an HLB value of 6 to 19, wherein the average number of polyoxyethylene units is 4 to 30). In another embodiment, the enhancer is an anionic surface active agent. In another embodiment, the enhancer is a cationic surface active, agent. In another embodiment, the enhancer is an ampholytic surface active agent. In one embodiment, zwitteruionic surfactants such as acylcarnitines serve as absorption enhancers.

In another embodiment, the amount of enhancer utilized in methods and compositions of the present invention is 0.1 mg/dosage unit. In another embodiment, the amount of enhancer is 0.2 mg/dosage unit. In another embodiment, the amount is 0.3 mg/dosage unit. In another embodiment, the amount is 0.4 mg/dosage unit. In another embodiment, the amount is 0.6 mg/dosage unit. In another embodiment, the amount is 0.8 mg/dosage unit. In another embodiment, the amount is 1 mg/dosage unit. In another embodiment, the amount is 1.5 mg/dosage unit. In another embodiment, the amount is 2 mg/dosage unit. In another embodiment, the amount is 2.5 mg/dosage unit. In another embodiment, the amount is 3 mg/dosage unit. In another embodiment, the amount is 5 mg/dosage unit. In another embodiment, the amount is 7 mg/dosage unit. In another embodiment, the amount is 10 mg/dosage unit. In another embodiment, the amount is 12 mg/dosage unit. In another embodiment, the amount is 15 mg/dosage unit. In another embodiment, the amount is 20 mg/dosage unit. In another embodiment, the amount is 30 mg/dosage unit. In another embodiment, the amount is 50 mg/dosage unit. In another embodiment, the amount is 70 mg/dosage unit. In another embodiment, the amount is 100 mg/dosage unit.

In another embodiment, the amount of enhancer is 0.1-1 mg/dosage unit. In another embodiment, the amount of enhancer is 0.2-1 mg/dosage unit. In another embodiment, the amount is 0.3-1 mg/dosage unit. In another embodiment, the amount is 0.5-1 mg/dosage unit. In another embodiment, the amount is 0.1-2 mg/dosage unit. In another embodiment, the amount is 0.2-2 mg/dosage unit. In another embodiment, the amount is 0.3-2 mg/dosage unit. In another embodiment, the amount is 0.5-2 mg/dosage unit. In another embodiment, the amount is 1-2 mg/dosage unit. In another embodiment, the amount is 1-10 mg/dosage unit. In another embodiment, the amount is 2-10 mg/dosage unit. In another embodiment, the amount is 3-10 mg/dosage unit. In another embodiment, the amount is 5-10 mg/dosage unit. In another embodiment, the amount is 1-20 mg/dosage unit. In another embodiment, the amount is 2-20 mg/dosage unit. In another embodiment, the amount is 3-20 mg/dosage unit. In another embodiment, the amount is 5-20 mg/dosage unit. In another embodiment, the amount is 10-20 mg/dosage unit. In another embodiment, the amount is 10-100 mg/dosage unit. In another embodiment, the amount is 20-100 mg/dosage unit. In another embodiment, the amount is 30-100 mg/dosage unit. In another embodiment, the amount is 50-100 mg/dosage unit. In another embodiment, the amount is 10-200 mg/dosage unit. In another embodiment, the amount is 20-200 mg/dosage unit. In another embodiment, the amount is 30-200 mg/dosage unit. In another embodiment, the amount is 50-200 mg/dosage unit. In another embodiment, the amount is 100-200 mg/dosage unit.

Each type and amount of enhancer represents a separate embodiment of the present invention.

In another embodiment, compositions of the present invention further comprise a coating that inhibits digestion of the composition in the stomach of a subject.

In one embodiment, coating inhibits digestion of the composition in the stomach of a subject. In one embodiment, the coated dosage forms of the present invention release drug when pH move towards alkaline range. In one embodiment, coating is a monolayer, wherein in other embodiments coating applied in multilayers. In one embodiment, coating is a bioadhesive polymer that selectively binds the intestinal mucosa and thus enables drug release in the attachment site. In one embodiment, the enteric coating is an enteric film coating. In some embodiment, coating comprises biodegradable polysaccharide, chitosan, aquateric aqueous, aquacoat ECD, azo polymer, cellulose acetate phthalate, cellulose acetate trimelliate, hydroxypropylmethyl cellulose phthalate, gelatin, poly vinyl acetate phthalate, hydrogel, pulsincap, or a combination thereof. In one embodiment, pH sensitive coating will be used according to the desired release site and/or profile as known to one skilled in the art.

In one embodiment, the coating is an enteric coating. Methods for enteric coating are well known in the art, and are described, for example, in Siepmann F, Siepmann J et al, Blends of aqueous polymer dispersions used for pellet coating: importance of the particle size. J Control Release 2005; 105(3): 226-39; and Huyghebaert N, Vermeire A, Remon J P. In vitro evaluation of coating polymers for enteric coating and human ileal targeting. Int J Pharm 2005; 298(1): 26-37. Each method represents a separate embodiment of the present invention.

In another embodiment, Eudragit®, an acrylic polymer, is used as the enteric coating. The use of acrylic polymers for the coating of pharmaceutical preparations is well known in the art. Eudragit Acrylic Polymers have been shown to be safe, and are neither absorbed nor metabolized by the body, but rather are eliminated.

In another embodiment, the coating is a gelatin coating. In another embodiment, microencapsulation is used to protect the exenatide against decomposition in the stomach. Methods for applying a gelatin coating and for microencapsulation are well known in the art. Each method represents a separate embodiment of the present invention.

In another embodiment, the coating is a film-coating. In another embodiment, the coating is ethylcellulose. In another embodiment, the coating is a water-based dispersion of ethylcellulose, e.g. hydroxypropylmethylcelullose (HPMC) E15. In another embodiment, the coating is a gastro-resistant coatings, e.g. a polymer containing carboxylic acid groups as a functional moiety. In another embodiment, the coating is a monolithic matrix. In another embodiment, the coating is a cellulose ether (e.g. hypromellose (HPMC). Each type of coating represents a separate embodiment of the present invention.

In another embodiment, a multiparticulate dosage forms is used to inhibit digestion of the composition in the stomach.

Each type of coating, dosage form, etc, that inhibits digestion of the composition in the stomach represents a separate embodiment of the present invention.

In another embodiment, the present invention provides a method for oral or rectal administration of a exenatide to a subject, whereby a substantial fraction of the exenatide retains its activity after absorption through an intestinal mucosal barrier or rectal mucosal bather of the subject, comprising administering orally or rectally to the subject a pharmaceutical composition comprising exenatide and a protease inhibitor, thereby orally or rectally administering exenatide to a subject. In another embodiment, the present invention provides a method for oral or rectal administration of a exenatide to a subject, whereby a substantial fraction of the exenatide retains its activity after absorption through an intestinal mucosal barrier or rectal mucosal barrier of the subject, comprising administering orally or rectally to the subject a pharmaceutical composition comprising exenatide and an omega-3 fatty acid.

In another embodiment, the present invention provides a method for treating diabetes mellitus in a subject, comprising administering orally or rectally to the subject a pharmaceutical composition comprising an exenatide and an omega-3 fatty acid, thereby treating diabetes mellitus.

In one embodiment, the diabetes mellitus is Type I diabetes. In another embodiment, the diabetes mellitus is Type II diabetes. In another embodiment, the diabetes mellitus is insulin-dependent diabetes. In another embodiment, the diabetes mellitus is non-insulin-dependent diabetes. In another embodiment, the diabetes mellitus is any other type of diabetes known in the art. Each possibility represents a separate embodiment of the present invention.

In one embodiment, six treatments a day of the exenatide composition are administered. In one embodiment, five treatments a day of the exenatide composition are administered. In another embodiment, four treatments a day of the exenatide composition are administered. In another embodiment, three treatments a day of the exenatide composition are administered. In another embodiment, two treatments a day are administered. In another embodiment, four treatments a day are administered. In another embodiment, one treatment a day is administered. In another embodiment, more than four treatments a day are administered. Each possibility represents a separate embodiment of the present invention.

In another embodiment, following oral or rectal exenatide administration to patients with type 2 diabetes, exenatide plasma concentrations rise rapidly and reach median peak plasma concentrations in 1.5-3 hours. In another embodiment, following oral or rectal administration exenatide concentrations are measurable for approximately 10 hours post-dose.

In another embodiment, following 2 days of exenatide oral or rectal administration a reduction in mean HbA1C is observed. In another embodiment, following 3 days of exenatide oral or rectal administration a reduction in mean HbA1C is observed. In another embodiment, following 4 days of exenatide oral or rectal administration a reduction in mean HbA1C is observed. In another embodiment, following 5 days of exenatide oral or rectal administration a reduction in mean HbA1C is observed.

In another embodiment, exenatide 20-300 mcg dosed administered before a meal results in reduction in postprandial glucose excursions. Additionally, the incidence of transient low blood glucose was higher when patients received exenatide administered after a meal. In another embodiment, exenatide 20-300 mcg should be administered within the 180 minute period before the meal. In another embodiment, exenatide 20-300 mcg should be administered within the 150 minute period before the meal. In another embodiment, exenatide 20-300 mcg should be administered within the 120 minute period before the meal. In another embodiment, exenatide 20-300 mcg should be administered within the 90 minute period before the meal. In another embodiment, exenatide 20-300 mcg should be administered within the 60 minute period before the meal. In another embodiment, exenatide 20-300 meg should be administered within the 30 minute period before the meal.

In another embodiment, Exenatide is indicated for treatment of type 1 diabetes mellitus. In another embodiment, Exenatide is indicated for treatment of type 2 diabetes mellitus (DM) in combination with metformin, and/or sulfonylureas in patients who have not achieved adequate glycemic control on maximally tolerated doses. In another embodiment, Exenatide is indicated for treatment of type 2 diabetes mellitus (DM) in combination with metformin. In another embodiment, Exenatide is indicated for treatment of type 2 diabetes mellitus (DM) in combination with sulfonylureas. In another embodiment, Exenatide of the invention is formulated in a single dosage four in combination with a sulfonylurea. In another embodiment, Exenatide of the invention is formulated in a single dosage form in combination with metformi.

In another embodiment, Exenatide formulations of the present invention are useful in view of their pharmacological properties. In another embodiment, Exenatide formulations of the present invention possess glucagon levels reduction activity. In another embodiment, Exenatide formulations of the present invention suppress glucagon secretion. In another embodiment, Exenatide formulations of the present invention suppress glucagon secretion, as evidenced by the ability to lower glucagon levels in animals and humans. In another embodiment, Exenatide formulations of the present invention are used to treat conditions or diseases that can be alleviated by reducing glucagon levels and suppressing glucagon secretion.

The compounds referenced above may form salts with various inorganic and organic acids and bases. Such salts include salts prepared with organic and inorganic acids, for example, HCl, HBr, $H_2SO_4$, $H_3PO_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g., sodium and potassium salts, and alkali earth salts, e.g., calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Obesity and Hypernutrition

In another embodiment, Exenatide formulations of the present invention are useful in preventing obesity. In another embodiment, Exenatide formulations of the present invention are useful in preventing excess adipose tissue. In another embodiment, Exenatide formulations of the present invention are useful in preventing health risks associated with enhanced food intake. In another embodiment, Exenatide formulations of the present invention are useful in preventing diseases associated with obesity such as Type 2 diabetes, increased cardiac risk, hypertension, atherosclerosis, degenerative arthritis, and increased incidence of complications of surgery involving general anesthesia. In another embodiment, Exenatide formulations of the present invention are useful in treating diseases associated with obesity such as Type 2 diabetes, increased cardiac risk, hypertension, atherosclerosis, degenerative arthritis, and increased incidence of complications of surgery involving general anesthesia. In another embodiment, Exenatide formulations of the present invention are useful in reducing the risk of developing diseases associated with obesity such as Type 2 diabetes, increased cardiac risk, hypertension, atherosclerosis, degenerative arthritis, and increased incidence of complications of surgery involving general anesthesia.

In another embodiment, Exenatide formulations of the present invention are useful in controlling body weight. In another embodiment, Exenatide formulations of the present invention are useful in maintaining body weight. In another embodiment, Exenatide formulations of the present invention are useful in reducing food intake. In another embodiment, Exenatide formulations of the present invention are useful in reducing food intake in obese subjects. In another embodiment, Exenatide formulations of the present invention are useful in decreasing the plasma glucose level. In another embodiment, Exenatide formulations of the present invention are useful in decreasing the plasma lipid level. In another embodiment, Exenatide formulations of the present invention are useful in preventing hypernutrition. In another embodiment, Exenatide formulations of the present invention are useful in treating hypernutrition.

In another embodiment, it can be appreciated that an effective means to reduce food intake is a major challenge and a superior method of treatment would be of great utility. Such a method, and compounds and compositions comprising Exenatide which are useful therefore, have been invented and are described and claimed herein. Any of the methods of the present invention may utilize, in various embodiments, any of the compositions of the present invention.

In another embodiment, the present invention provides a composition for oral or rectal administration of exenatide, comprising an exenatide protein and a protease inhibitor, whereby a substantial fraction of the exenatide retains the enzymatic activity after absorption through an intestinal mucosal barrier of a subject. In another embodiment, the present invention provides a composition for oral or rectal administration of exenatide, comprising an exenatide protein and an enhancer, whereby a substantial fraction of the exenatide retains the enzymatic activity after absorption through an intestinal mucosal barrier of a subject. In another embodiment, the present invention provides a composition for oral or rectal administration of exenatide, comprising an exenatide protein and an omega-3 fatty acid, whereby a substantial fraction of the exenatide retains the enzymatic activity after absorption through an intestinal mucosal barrier of a subject.

In one embodiment, the present invention provides the use of exenatide and a protease inhibitor in the manufacture of a medicament for oral or rectal administration of exenatide to a subject, whereby a substantial fraction of exenatide retains its activity after absorption through an intestinal mucosal barrier of the subject. In one embodiment, the present invention provides the use of exenatide and an enhancer in the manufacture of a medicament for oral or rectal administration of exenatide to a subject, whereby a substantial fraction of exenatide retains its activity after absorption through an intestinal mucosal barrier of the subject. In one embodiment, the present invention provides the use of exenatide and an omega-3 fatty acid in the manufacture of a medicament for oral or rectal administration of exenatide to a subject, whereby a substantial fraction of exenatide retains its activity after absorption through an intestinal mucosal barrier of the subject.

In one embodiment, the present invention provides the use of an exenatide protein and a protease inhibitor in the manufacture of a medicament for treating diabetes mellitus in a subject. In one embodiment, the present invention provides the use of an exenatide protein and an enhancer in the manufacture of a medicament for treating diabetes mellitus in a subject. In one embodiment, the present invention provides the use of an exenatide protein and an omega-3 fatty acid in the manufacture of a medicament for treating diabetes mellitus in a subject.

In another embodiment, different constituents of compositions of the present composition are absorbed at different rates from the intestinal lumen into the blood stream. The absorption of the bile acid, in one embodiment, is significantly faster than the absorption of exenatide.

For this reason, in another embodiment, a drug regimen involving ingestion of a pair of pills at spaced intervals, e.g., a second pill containing a higher concentration of enhancer is taken at a defined interval (e.g. 30 minutes) after the first pill. In another embodiment, certain of the constituents are microencapsulated to enhance the absorption of the exenatide into the system.

In one embodiment, a treatment protocol of the present invention is therapeutic. In another embodiment, the protocol is prophylactic. Each possibility represents a separate embodiment of the present invention.

In another embodiment, the present invention provides oral or rectal administration of exenatide which is comparable to previous injectable dosage forms of exenatide. In another embodiment, the present invention provides superior oral or rectal administration of exenatide compared to previous injectable dosage forms of exenatide. In another embodiment, oral or rectal administration of exenatide is cheaper than injectable dosage forms of exenatide. In another embodiment, oral or rectal administration of exenatide provides better compliance than injectable dosage forms of exenatide. In another embodiment, oral or rectal administration of exenatide provides fewer side effects than injectable dosage forms of exenatide.

In another embodiment, solid carriers/diluents for use in methods and compositions of the present invention include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In another embodiment, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCL, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants. Each of the above excipients represents a separate embodiment of the present invention.

In some embodiments, the dosage forms of the present invention are formulated to achieve an immediate release profile, an extended release profile, or a delayed release profile. In some embodiments, the release profile of the composition is determined by using specific excipients that serve for example as binders, disintegrants, fillers, or coating materials. In one embodiment, the composition will be formulated to achieve a particular release profile as known to one skilled in the art.

In another embodiment, the oral or rectal formulation of the present invention is further formulated to accomplish sustained release of Exenatide. In another embodiment, the oral or rectal formulation of the present invention is further formulated to accomplish immediate release of Exenatide. In another embodiment, the oral or rectal formulation of the present invention is further formulated to accomplish slow release of Exenatide. In another embodiment, the oral or rectal formulation of the present invention is further formulated to accomplish a combination of sustained and immediate release of Exenatide. In another embodiment, the release rate of Exenatide can be manipulated by various foimulatory methods known to one of skill in the art of the invention.

In one embodiment, the composition is formulated as an oral dosage form. In one embodiment, the composition is a solid oral dosage form comprising tablets, chewable tablets, suppositories, or capsules. In one embodiment the capsules are soft gelatin capsules.

In other embodiments, controlled- or sustained-release coatings utilized in methods and compositions of the present invention include formulation in lipophilic depots (e.g. fatty acids, waxes, oils).

The compositions also include, in another embodiment, incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance. In another embodiment, particulate compositions of the active ingredients are coated with polymers (e.g. poloxamers or poloxamines)

In another embodiment, the compositions containing the exenatide and omega-3 fatty acid are delivered in a vesicle, e.g. a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

The preparation of pharmaceutical compositions that contain an active component, for example by mixing, granulating, or tablet-forming processes, is well understood in the art. The active therapeutic ingredient is often mixed with excipients that are pharmaceutically acceptable and compatible with the active ingredient. For oral administration, the active ingredients of compositions of the present invention are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions.

In another embodiment, the formulation of the present invention further comprises a base. In another embodiment, the base used in the pharmaceutical composition of this invention may be those which are known as bases of suppositories for intrarectal administration. In some embodiments, base include oils and fats comprising triglycerides as main companothernts such as cacao butter, palm fat, palm kernel oil, coconut oil, fractionated coconut oil, lard and WITEPSOL®, waxes such as lanolin and reduced lanolin; hydrocarbons such as Vaseline, squalene, squalane and liquid paraffin; long to medium chain fatty acids such as caprylic acid, lauric acid, stearic acid and oleic acid; higher alcohols such as lauryl alcohol, cetanol and stearyl alcohol; fatty acid esters such as butyl stearate and dilauryl malonate; medium to long chain carboxylic acid esters of glycerin such as triolein and tristearin; glycerin-substituted carboxylic acid esters such as glycerin acetoacetate; and polyethylene glycols and its derivatives such as macrogols and cetomacrogol. They may be used either singly or in combination of two or more.

In some embodiments, the composition of this invention may further include a surface-active agent, preservative, and coloring agent, which are ordinarily used in suppositories.

In another embodiment, the unit dosage forms of the pharmaceutical composition of this invention include a solid suppository having as a base a solid fat which when administered to the rectum, becomes flowable within the rectum, such as cacao butter and WITEPSOL, a solid suppository having as a base a hydrophilic solid substance which becomes flowable in the rectum in the same way, such as macrogol, and a gelatin capsule suppository having a nomally liquid substance (liquid at room temperature) such as neutral fatty acid triglycerides and vegetable oils as a base and coated with a gelatin film.

Each of the above additives, excipients, formulations and methods of administration represents a separate embodiment of the present invention.

In one embodiment, the term "treating" refers to curing a disease. In another embodiment, "treating" refers to preventing a disease. In another embodiment, "treating" refers to reducing the incidence of a disease. In another embodiment, "treating" refers to ameliorating symptoms of a disease. In another embodiment, "treating" refers to inducing remission. In another embodiment, "treating" refers to slowing the progression of a disease.

EXPERIMENTAL DETAILS SECTION

Animals

Male beagle dogs weighing about 9 kg were used for all experiments described hereinbelow.

Example 1

Protection of Exenatide from Proteases and Successful Administration Via the Duodenum in Dogs Materials and Experimental Methods Formulations (1) A formulation containing 150 milligram (mg) Na-EDTA (Sigma-Aldrich, St. Louis, Mo.), 125 mg soybean trypsin inhibitor (SBTI; Sigma), 50 µg exenatide, and 0.8 milliliter (ml) fish oil was prepared.

A formulation containing 150 milligram (mg) Na-EDTA (Sigma-Aldrich, St. Louis, Mo.), 125 mg soybean trypsin inhibitor (SBTI; Sigma), 100 µg exenatide, and 0.8 milliliter (ml) fish oil was prepared.

(3) A formulation containing 150 milligram (mg) Na-EDTA (Sigma-Aldrich, St. Louis, Mo.), 125 mg soybean trypsin inhibitor (SBTI; Sigma), 0.8 milliliter (ml) fish oil was prepared.

Results

To test whether exenatide can be protected from proteases and absorbed via the duodenum, formulation 1 (treatment) or 3 (control) were administered directly to the duodenum of about 9 kg beagle dogs or by an endoscope to about 16 kg pigs.

All dogs and pigs were administered 40 ml of 50% glucose solution. Blood glucose was measured every 5 minutes following administration. As depicted below in Table 1, blood glucose levels were significantly reduced in response to exenatide.

Figure 3:
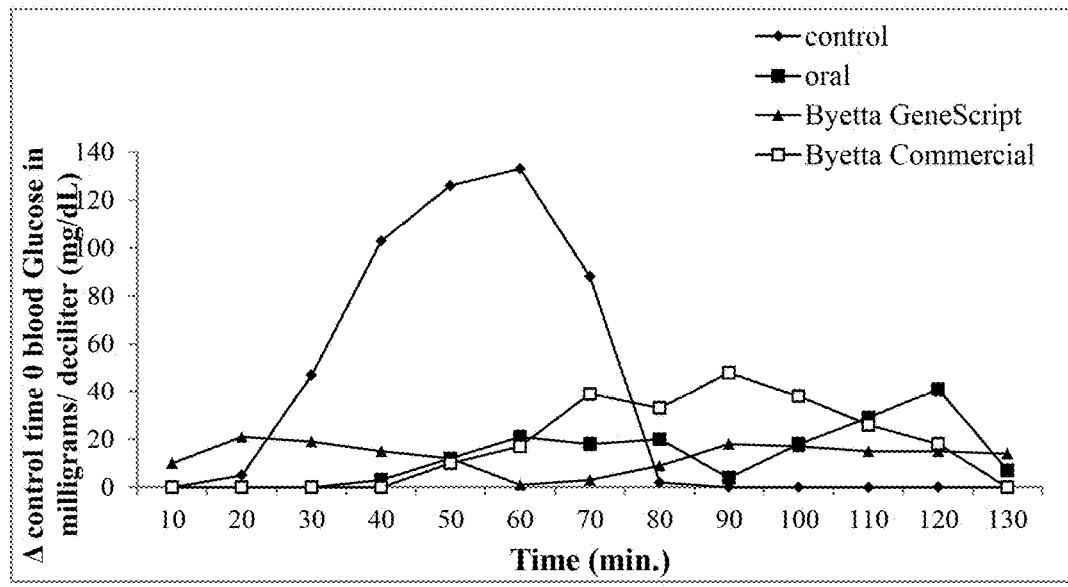
FIG. 3 is a graph comparing the blood glucose lowering effect of an Exendin-4 in an oral dosage form (100 µg Exendin 4), control, and injectable dosage forms (2.5 µg Byetta GeneScript and 2.5 µg Byetta Commercial) in dogs (the concentration of blood glucose at time 0 was deducted from each value obtained at a given time).

The ability of formula 1 to substantially reduce blood glucose levels is also shown in FIG. 1 in dogs. Similar results were obtained in pigs. Moreover, FIG. 3 shows that an oral dosage form of Exendin-4_can replace injectable dosage forms of Exendin-4_(see Example 2) in reducing blood glucose levels.

TABLE 1

Blood glucose concentrations following administration of exenatide to the duodenum in experiment #1.

| Time (min) | Glucose in milligrams/deciliter (mg/dL) in dogs treated with formulation 1-Treatment | Glucose in milligrams/deciliter (mg/dL) in dogs treated with formulation 3-Control |
|---|---|---|
| 0 | 69 | 69 |
| 10 | 93 | 97 |
| 20 | 89 | 131 |
| 30 | 93 | 159 |
| 40 | 111 | 156 |
| 50 | 94 | 139 |
| 60 | 103 | 134 |
| 70 | 104 | 112 |
| 80 | 118 | 117 |
| 90 | 105 | 84 |
| 100 | 90 | 88 |
| 110 | 94 | 80 |
| 120 | 92 | 73 |

Thus, oral compositions comprising a protease inhibitor and Na-EDTA can protect exenatide from proteases in the small intestine and enable direct absorption of orally administered exenatide.

Example 2: Injectable Dosage Forms Compared to Rectal and Oral Dosage Forms

Materials and Experimental Methods

Formulation

The following formulations were prepared:

(1) An injectable formulation comprising 2.5 µg commercial byetta.

(2) An injectable formulation comprising 2.5 µg GeneScript (Piscataway, N.J.) byetta.

(3) An oral formulation containing 150 milligram (mg) Na-EDTA (Sigma-Aldrich, St. Louis, Mo.), 125 mg soybean trypsin inhibitor (SBTI; Sigma), 50 µg exenatide (GeneScript (Piscataway, N.J.)) and 0.8 milliliter (ml) fish oil.

(4) An oral formulation containing 150 milligram (mg) Na-EDTA (Sigma-Aldrich, St. Louis, Mo.), 125 mg soybean trypsin inhibitor (SBTI; Sigma), 0.8 milliliter (ml) fish oil.

(5) A hard gelatin capsule (rectal) containing 150 milligram (mg) Na-EDTA (Sigma-Aldrich, St. Louis, Mo.), 125 mg soybean trypsin inhibitor (SBTI; Sigma), 50 µg exenatide (GeneScript (Piscataway, N.J.)) and in 0.8 milliliter (ml) fish oil.

Results

To test the effectiveness of oral and rectal formulations comprising exenatide, oral and rectal formulations were compared to commercially available injectable formulations.

All dogs were administered 40 ml of 50% glucose solution. Blood glucose was measured every 5 minutes following administration.

Figure 2:
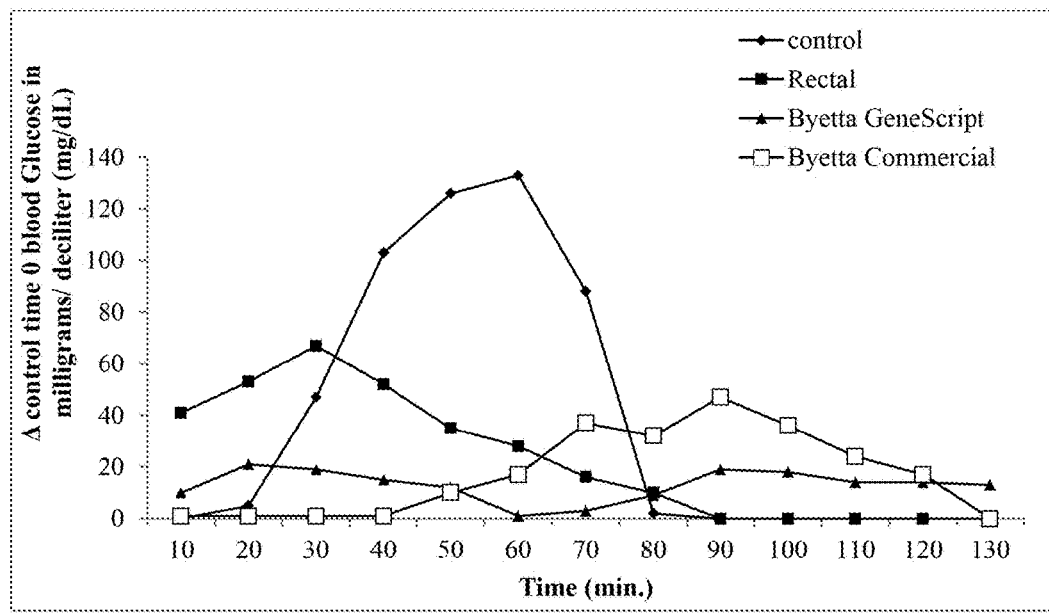
FIG. 2 is a graph comparing the blood glucose lowering effect of an Exendin-4 in a rectal dosage form (hard gelatin capsule, 100 µg Exendin 4), injectable dosage forms (2.5 µg Byetta GeneScript and 2.5 µg Byetta Commercial), and control in dogs, the values are calculated as Δ time 0 (the concentration of blood glucose at time 0 was deducted from each value obtained at a given time).

The results obtained show that oral (FIGS. 1 and 3) and rectal (FIG. 2) dosage forms comprising Exendin-4 can unexpectedly replace injectable dosage forms comprising Exendin-4_in terms of controlling blood glucose levels for 2 hours after glucose load.

These results further confirm the results of Example 1, showing that compositions comprising a protease inhibitor and Na-EDTA can protect exenatide from proteases in the small intestine and enable direct absorption of orally administered exenatide.

The Exendin-4_used for the oral and rectal dosage forms was obtained from GeneScript. The results presented (FIGS. 2 and 4) show that Exendin-4_purchased from GeneScript is effective as the commercial Exendin-4 (Eli Lilly, USA). In conclusion, the oral and/or rectal routes of administration are favorable over the injectable route of administration for many reasons that are known to one of skill in the art. The unexpected results presented herein demonstrate the ability to effectively administer Exendin-4_via an oral or rectal route of administration.

Example 3: Enteral Administration of Exenatide-4; Proof of Concept Pharmacodynamic Study in Dogs with a Formulation which Facilitates the Absorption of Exenatide-4 Across Biological Membranes Materials and Experimental Methods Study was conducted in 4 beagle dogs with an average weight of 10 kg. All the dogs had a cannula residing in the jejunum through which the drug was administered. After an overnight fast, the dogs were given different doses of oral GLP-1 analogue or sc injection of the analogue. Absorption of the GLP-1 analogue was assessed by measuring the effect on glucose excursion following an oral glucose load. Control experiment consisted of oral dosing without administration of GLP-1 analogue. The interval between oral administration and the oral glucose load was 30 minutes. The primary efficacy end point was the glucose excursion above the pre-OGTT glucose level over a 150 min interval (incremental area under the curve $(AUC)_{0-150\ min}$).

Results

Direct jejunal instillation of GLP-1 analogue significantly (ss) curbed glucose excursion, post glucose load (both in comparison to placebo and among the separate groups)

Figure 4:
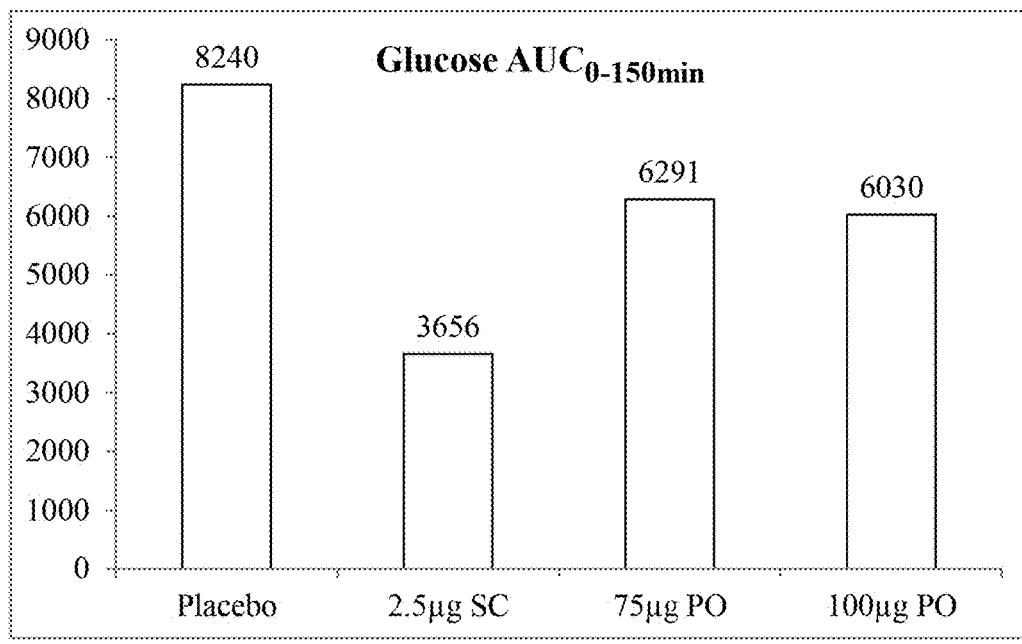
FIG. 4 is a bar graph showing the glucose excursion above the pre-OGTT glucose level over a 150 min interval (incremental area under the curve $(AUC)_{0-150}$).

Results are shown in Table 2 and FIG. 4.

TABLE 2

| OGTT—Glucose $AUC_{0-150\ min}$ Mean ± SD | |
|---|---|
| Placebo | 8906 ± 1508 |
| GLP-1 2.5 µg sc | 3656 ± 510 |
| GLP-1 75 µg PO | 6292 ± 1043 |
| GLP-1 100 µg PO | 5085 ± 931 |

Oral delivery of proteins and peptide drugs remains a major challenge because of their unique physico-chemical and biologic properties. As demonstrated herein the presented proprietary technology can effectively and reliably transport macromolecules including polypeptides and proteins such as exenatide across biological membranes. Moreover, unexpectedly, the native compound retained its biological activity on reaching the systemic circulation.

Specifically, in the current study in dogs the results clearly demonstrate that an oral GLP-1 analogue, exenatide, when administered before a meal can blunt meal induced glycemic excursion by about 40% as compared to parenteral exenatide 50% blunting capacity. Pd effects are commonly used in a semi-quantitative way to establish GLP-1 levels in studies assessing DPP IV inhibition. In this study it have been unexpectedly demonstrated that the GLP-1 analogue exenatide can be created in an oral dosage form and that it could be ingested by the patient shortly before a meal. These two qualities in a drug significantly facilitate its acceptance among, patients and foster higher patient compliance and adherence to the medication.

The results of this study in dogs showed that GLP-1 analogue exenatide when combined with the delivery enhancers and formulated in a capsule is absorbed and results in significant blunting of glucose excursion after an oral OGTT. The Pharmacodynamic response to oral exenatide ingestion was robust and reproducible and the short interval between capsule ingestion and meal suggests that a practical and patient friendly oral dosage form can be created. As of now the only incretin mimetics available as oral medication are the DPP IV inhibitors. An oral dosage form of GLP-1 analogues will broaden the choice of available drugs from this important class of antihyperglycemic medication.

Example 4

Oral Administration of Pills Containing Exenatide and a Protease Inhibitor

Preparation of Tablet Cores

Tablet cores comprising exenatide and a protease inhibitor are prepared using methods well known in the art.

Coating

The coating may be any delayed release coating known in the art. For example, the coating may be a polymer composed of the following ingredients:
  4 mg Eudragit L-100 (Polymer of Acrylic and Methacrylic Acid Esters)
  4 mg Talc NF
  0.4 mg Polyethylene Glycol 6000 NF In one embodiment, a solution of the enteric coated polymer is prepared by dissolving the polymer in a methylene chloride+isopropyl alcohol mixture. The tablets are coated by spraying the solution within a mildly warmed jar under constant agitation. The solvent vapors are continuously aspirated.

Measurement of Levels and Activity of Recombinant Exenatide in Subjects' Plasma

Levels of C peptide are measured as well, to determine the relative contributions of endogenous and exogenous exenatide to observed rises in exenatide levels.

Results

A mixture of Na-EDTA, SBTI, and exenatide and fish oil is formulated into tablet or capsule cores, coated with an enteric coating or gelatin coating, and administered to human subjects. Blood glucose levels of the subjects are measured periodically as described in the previous Examples. In addition, the subjects' plasma levels of recombinant exenatide and its activity are tested. The coated pills are shown to deliver functional exenatide to the subjects, and the exenatide significantly lowers their blood glucose levels, showing that active exenatide can be delivered to the bloodstream via oral administration. Different types of commercially available delayed release coatings are tested to determine which coating provides the best delivery of exenatide, and this coating is used in subsequent Examples.

Example 5

Optimization of Source of Omega-3 Fatty Acids

Various omega-3 fatty acids or sources of omega-3 fatty acids (e.g. those listed above in the specification) are compared for their ability to preserve exenatide following oral administration in methods and compositions of the present invention. Exenatide tablets or capsules are formulated as described in the above Examples, except that the exenatide is combined with alternate source instead of in fish oil. The most effective source of omega-3 fatty acids is used in subsequent Examples.

Example 6

Optimization of Protease Inhibitors

Various protease inhibitors (either non-toxic or having an acceptable toxicity profile; e.g. those listed above in the specification) are compared for their ability to preserve exenatide following oral administration in methods and compositions of the present invention. Exenatide tablets or capsules are formulated as described in the above Examples, except that the alternate protease inhibitors are substituted for SBTI. Amounts of the protease inhibitors are also varied, to determine the optimal amounts. The most effective protease inhibitor/amount is used in subsequent Examples.

Example 7

Optimization of Enhancer

Various enhancers (e.g. those listed above in the specification) are compared for their ability to facilitate absorption of exenatide following oral administration in methods and compositions of the present invention. Exenatide tablets or capsules are formulated as described in the above Examples, except that the alternate enhancers are substituted for EDTA. Amounts of the enhancers are also varied, to determine the optimal amounts. The most effective enhancer/amount is used in subsequent experiments.

Example 8

Optimization of Type and Amount of Exenatide

Various types and amounts of exenatide e.g. those listed above in the specification) are compared for their ability to regulate blood sugar in methods and compositions of the present invention. Exenatide tablets or capsules are formulated as described in the above Examples, except that the type and amount of exenatide is varied. The most effective type/amount of exenatide is used in clinical trials.

What is claimed is:

1. A method for slowing the progression and/or ameliorating the symptoms of diabetes mellitus in a subject, comprising administering orally to said subject a pharmaceutical composition comprising an exenatide having at least 95% identity to HGEGTFTSDLSKQMEEEAVR-LFIEWLKNGGPSSGAPPPS (SEQ ID NO: 1), wherein the exenatide has glucagon-like peptide (GLP-1) agonist activity, a protease inhibitor selected from Soybean Trypsin Inhibitor (SBTI) and aprotinin, EDTA, and an omega-3 fatty acid, thereby slowing the progression and/or ameliorating the symptoms of diabetes mellitus, wherein the composition does not comprise both SBTI and aprotinin.

2. The method of claim 1, wherein said omega-3 fatty acid is derived from fish oil.

3. The method of claim 1, wherein said protease inhibitor is soybean trypsin inhibitor (SBTI).

4. The method of claim 1, wherein said pharmaceutical composition further comprises a coating that inhibits digestion of said composition in a stomach of a subject.

5. The method of claim 4, wherein said coating is an enteric coating.

6. The method of claim 1, wherein said pharmaceutical composition further comprises a gelatin coating.

7. The method of claim 1, wherein said protease inhibitor is aprotinin.

8. The method of claim 1, wherein the sequence of said exenatide is identical to SEQ ID NO: 1.

9. The method of claim 1, wherein said omega-3 fatty acid is provided in the form of a fish oil.

10. The method of claim 1, wherein the progression of diabetes mellitus is slowed in the subject.

11. The method of claim 1, wherein the symptoms of diabetes mellitus are ameliorated in the subject.

* * * * *

```
                        SEQUENCE LISTING

<160> NUMBER OF SEQ ID NOS: 1

<210> SEQ ID NO 1
<211> LENGTH: 39
<212> TYPE: PRT
<213> ORGANISM: Heloderma suspectum

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```